United States Patent [19]
Carisse

[11] Patent Number: 5,888,496
[45] Date of Patent: Mar. 30, 1999

[54] **MICROBIAL PEST CONTROL AGENT AGAINST THE APPLE SCAB PATHOGEN *VENTURIA INAEQUALIS***

[75] Inventor: Odile Carisse, St-Luc, Canada

[73] Assignee: Her Majesty the Queen in Right of Canada, as represented by Agriculture and Agri-Food Canada, Quebec, Canada

[21] Appl. No.: 889,628

[22] Filed: Jul. 8, 1997

[51] Int. Cl.⁶ .............................. A01N 63/00; C12P 1/02
[52] U.S. Cl. ................... 424/93.5; 435/171; 435/254.1; 435/255.1
[58] Field of Search ................. 424/93.5; 435/255.1, 435/254.1, 171

[56] References Cited

U.S. PATENT DOCUMENTS

| | | | |
|---|---|---|---|
| 3,284,287 | 11/1966 | D'Amico | 167/22 |
| 3,346,592 | 10/1967 | Dunbar | 260/333 |
| 5,143,932 | 9/1992 | Jautelat et al. | 514/383 |

OTHER PUBLICATIONS

The Screening of Potential Fungal Antagonists of Pseudothecial Formation by the Apple Scab Pathogen, Vincent Philion, Masters Thesis, Dec., 1994.

*Primary Examiner*—Herbert J. Lilling
*Attorney, Agent, or Firm*—Thompson Hine & Flory LLP

[57] ABSTRACT

Apple scab, caused by the fungal pathogen *Venturia inaequalis*, is considered to be the most important single disease of apple worldwide and one of the most costly to control. Currently, the strategy for apple scab control relies on multiple applications of fungicides, often 8 to 12 fungicide sprays each growing season. These sprays represent an appreciable input of costs to growers and additionally, they can have a substantial impact on the environment. A new microbial pest control agent belonging to the genus Microsphaeropsis has been isolated. The application of this agent after harvest inhibits the formation of pseudothecia of *V. inaequalis* and consequently reduces the amount of primary inoculum the following spring which will result in a reduced spraying schedule.

5 Claims, 5 Drawing Sheets

Top view

Side view

MICROBIAL PEST CONTROL AGENT AGAINST THE APPLE SCAB PATHOGEN *VENTURIA INAEQUALIS*

The present invention relates to a microbial pest control agent active against *Venturia inaequalis*.

BACKGROUND OF THE INVENTION

After years of research and treatment, apple scab, caused by *Venturia inaequalis* (CKE.) Wint., is economically the worst disease of apple trees (*Malus domesticus* L.) worldwide (Agrios, 1988). Much research has been devoted to the control of primary infections, and it has yielded very costly and ecologically questionable spraying schedules (Funt, 1990). These sprays represent an appreciable cost to growers and can have a substantial indirect impact on the environment. Development of fungicide resistance in the pathogen population is also threatening apple production. Thus it is essential to develop an ecologically and environmentally friendly alternative control strategy for apple scab.

In cold temperature regions, the fungal pathogen *V. inaequalis* overwinters as a saprophyte and to a significant extent only as incipient pseudothecia (sexual structures) in fallen apple leaves on the orchard floor. Pseudothecia, initiated during fall or winter, mature in the spring to produce ascospores which serve as primary inoculum for the initial infections (Ellis 1990). Thus, the overwintering stage is one weak link in the life cycle of the fungus. If the pathogen could be killed or seriously weakened in the leaf litter, the primary inoculum available in the spring would be substantially reduced.

Ascospore discharged from leaves are dispersed by wind to expanding floral primordia and unfolding leaves. Floral, leaf, and fruit tissues are much more susceptible when young than when mature. Early infection, particularly of floral structures, by primary inoculum (ascospores) is thus extremely significant in the epidemiology of this disease because the fungus becomes established in a favourable location for secondary infection of the developing fruit and leaves. The critical time for the development of apple scab is from the opening of fruit buds until petal fall. If the disease can be suppressed during this time, its later management is usually easier. Thus, this period is the second key stage in the life cycle for the disease control.

After the host penetrates, a fungal stoma eventually develops between the cuticle and the outer walls of the epidermal cells. This stroma produces conidiophores which rupture the host cuticle. Conidia borne from these conidiophores are dispersed by the movement of wind and rain to susceptible leaves and fruit where secondary infection occurs. This secondary infection repeats itself until leaf fall in the autumn. When the pathogen, *V. inaequalis*, infects developing fruit, it causes corky lesions and deformations, reducing yields and making fruit unmarketable. The overwintering saprophytic stage is then re-initiated.

Early attempts to use urea to reduce the primary inoculum of *V. inaequalis* was reported in the 1960's (Cook, 1969). Since then a lot of attention was focused on safe methods for the reduction of the primary inoculum and less attention was devoted to methods which employed dangerous chemicals such as DNOC and lead arsenate. Cultural methods aimed at destroying the leaves such as mulching and tilling were also successfully used in the past.

Certain organisms, mainly fungal isolates, when applied in autumn on fallen leaves will inhibit pseudothecial formation and thus reduce ascospore production in the following spring. Heye (1982) found a fungus, *Athelia bombacina*, which completely inhibited the formation of pseudothecia on sterile discs (Heye and Andrews, 1983). This antagonist was also tested under field conditions. However, results are incomplete since it was not evaluated during the whole ascospore ejection season (Miedtke and Kennel, 1990).

Thus, there is a need for a biological control agent against *V. inaequalis*, which can be used on a commercial scale.

SUMMARY OF THE INVENTION

The present invention relates to a microbial pest control agent active against *Venturia inaequalis*. More specifically the present invention is directed to a microbial pest control agent of the genus Microsphaeropsis.

In one embodiment of the present invention there is provided an substantially pure isolate of a species of the genus Microsphaeropsis, which is effective in controlling apple scab caused by *V. inaequalis*.

In a further embodiment of the present invention there is provided a method of controlling apple scab caused by *V. inaequalis* comprising applying an effective amount of an isolate of a species of the genus Microsphaeropsis.

The present invention also provides a method of purifying an extract from the isolate of a species of the genus Microsphaeropsis, which is effective in controlling apple scab caused by *V. inaequalis*.

A further embodiment of the present invention is directed to a substantially purified extract from an isolate of a species of the genus Microsphaeropsis, which is effective in controlling apple scab caused by *V. inaequalis*.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
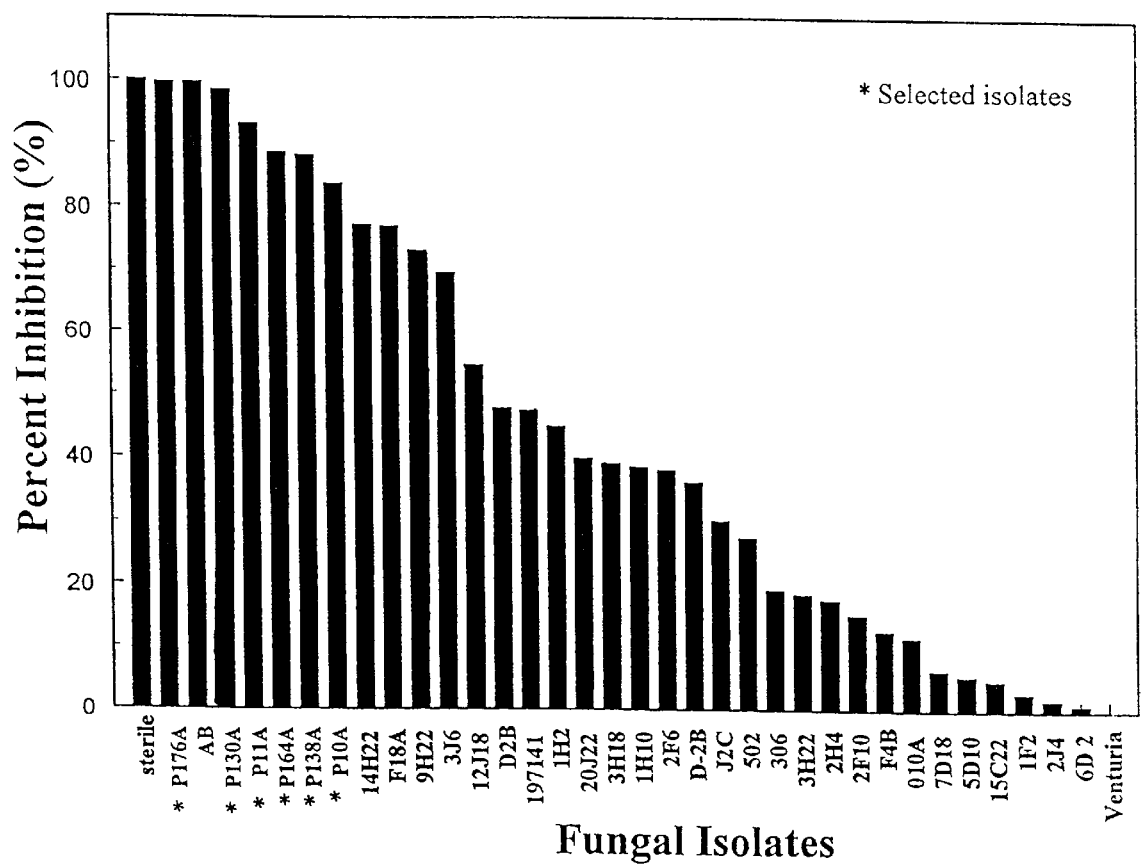
FIG. 1: The effect of different fungal isolates on the ascospore production of *V. inaequalis*; inoculation of *V. inaequalis* with mycelium (the "M" experiment in Example 1).
Figure 2:
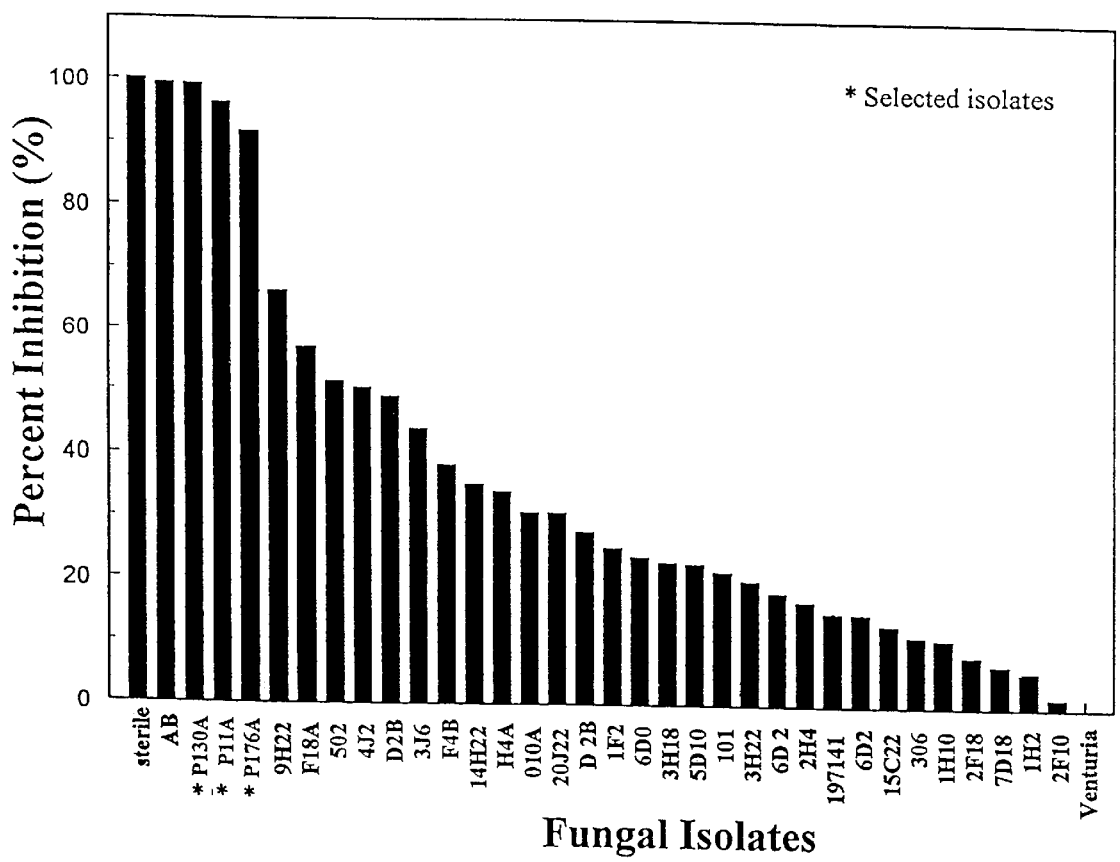
FIG. 2: The effect of different fungal isolates on the ascospore production of *V. inaequalis*; inoculation of *V. inaequalis* with conidia (the "C" experiment in Example 2).

The present invention relates to a microbial pest control agent active against *Venturia inaequalis*. More specifically the present invention is directed to a microbial pest control agent of the genus Microsphaeropsis.

Samples of natural fungal microflora were collected from an abandoned apple orchard. Dead leaves were collected from the ground after snow melt and the leaves were placed in appropriate growth media to encourage the growth of any natural fungal microflora occurring on the leaves. A number of isolates were collected and tested for their ability to degrade apple leaf tissue, inhibit pseudothecia or ascospore production of *V. inaequalis*. As mentioned above, if pseudothecia or ascospore production of *V. inaequalis* could be reduced then the present reliance on chemical spays could also be reduced.

In the present invention six samples: P176A, P130A, P11A, P164A, P138A and P10A significantly reduced ascospore production of V. inaequalis with conidia. Three isolates P176A, P130A and P11A significantly reduced ascospore production of V. inaequalis with mycelium. The first three isolates were common to both sets.

In one embodiment of this present invention two of the possible isolates, based on morphological characteristics, have been determined to belong to the genus Microsphaeropsis. Suitable isolates, which have been identified according to the present invention include, but are not limited to, isolates identified as P130A and P176A. In one embodiment of the present invention isolates P130A and P176A were consistently in the top ten in tests to determine leaf rheology, ascospore and pseudothecia reduction. One isolate of the present invention P130A has been deposited with the American Type Culture Collection on May 23, 1997 under Assession Number 74412.

One aspect of the present invention involves a method of controlling and or reducing the incidence of V. inaequalis infestation and thus reducing the amount of chemical spraying of the apple orchard. In this aspect of the invention a suitable amount of the microbial pest control agent comprising a single isolate is applied after harvest to inhibit the formation of pseudothecia and ascospore of V. inaequalis, and consequently reduce the amount of primary inoculum the following spring. Thus according to this aspect of the invention the microbial pest control agent comprises one isolate identified as P130A.

The isolates of the present invention can be used along or together with suitable carriers. Any aqueous material that does not adversely effect the effectiveness of the isolate could be mixed with the isolate and used as the microbial pest control agent. Any effective amount of the microbial pest control agent can be used. The most effective amount can be determined empirically by persons skilled in the art. Examples of effective amounts can range from $2 \times 10^5$ to $6 \times 10^5$ conidia per ml. The suspension of conidia can be applied at a dose of from about 1000L/ha to about 1500L/ha or from about 1L per tree to about 1.5L per tree. The invention is of course not limited to these specific examples, as persons skilled in the art could make appropriate amendments as required.

In a further embodiment of the present invention, the active fraction from the isolate is partially purified. In this aspect of the invention the isolate was grown in a liquid medium and the broth collected after an appropriate growth period. The liquid media was subjected to a solvent extraction, to obtain a solvent extract. The solvent extract was then dried and resuspended in a small volume of solvent. In one example of the present invention chloroform is used to obtain the solvent extract. The dried solvent extract can be resuspended in methanol or chloroform for example. According to this aspect of the invention two active fractions were identified, one with an approximate $R_f$ value of 0.65 and one with approximate $R_f$ value of 0.95.

In a further embodiment of the present invention the solvent extract can be further purified by silicic acid column chromatography. The solvent extract, in one example the chloroform extract, was applied to a column of silica gel silicic acid and eluted with steps of increasing concentration of methanol in chloroform. From such a column four fraction were identified. Of these four fractions only one, FII, showed strong antifungal activity.

In yet a further embodiment of the present invention the active fraction (FII), purified from the silica gel column as described above can be further purified by preparative thin layer chromatography. A number of fractions were identified, of which fractions F-II2 and FII3a were found to have antifungal activity.

Thus the present invention is also directed to any one of these partially purified extracts of the isolates of the present invention. One or more of these partially purified extract can be used alone or together with one or more extracts, any of which can be added to any acceptable carrier prior to use.

Thus according to the present invention, any one of these partially purified fractions from the isolates of the present invention could be used to inhibit the formation of pseudothecia and ascospore of V. inaequalis. As with the isolates, the partially purified fractions would be applied after harvest to inhibit the formation of pseudothecia and ascospore of V. inaequalis in the following spring.

While this invention is described in detail with particular reference to preferred embodiments thereof, said embodiments are offered to illustrate but not to limit the invention.

EXAMPLES

Example 1

Isolation and Characterization of the Microbial Pest Control Agent

Sampling was done in an apple (Malus pumila Mill var McIntosh) orchard, which had been abandoned for more than five years, to ensure that no fungicide treatment or residues would affected the natural fungal microflora. Dead apple leaves lying on the ground were collected for a three day period after snow melt. Arbitrarily chosen leaves were placed in glass petri plates of 9 cm diameter containing a sheet of Whatman filter paper saturated with distilled water. The petri plates were incubated at −2° C. for two to three weeks, four plates per temperature. The leaves were observed under a dissecting microscope and each mass of spores, fruiting bodies or mycelia was picked up and placed on half-strength V8 agar media amended with 100 μg/ml of chlorotetracycline and 200 μg/ml of streptomycin. The isolate was transferred to V8 medium (Calcium carbonate, 3 g; bacto agar, 15 g; V-8 juice, 100 ml; and distilled $H_2O$; 900 ml).

Resulting colonies were cream color, with a cottony aspect, on both sides of the colonies. Growth was relatively slow on V-8 agar (5 cm in 14 days) and the color of the media turned brown. The isolate produced dark brown to black pycnidia on different agar media after a few weeks, and after 10 days when inoculated on apple leaves or in soil. Droplets of black liquid containing conidia may ooze out by the pycnidia ostiole. A description of the isolate was as follows:

Mycelium: brown, septate, branched

Conidiomata: pycnidia partially superficial, black, globose, ostiolate

Ostiol: simple, circular

Conidiophore: absent

Conidiogenous cells: Enteroblastic, phialidic

Conidia: pale brown, aseptate, smooth and thin-walled, guttulate, no appendices, cylindrical to elliptical (4–6 μ×2–4 μ)

As a result of this description the isolate (P130A) was determined to belong to the genus Microsphaeropsis. As previously discussed, this strain has been deposited with the American Type Culture Collection on May 23, 1997, under ATCC designation number 74412.

When comparing conidia of P130A with those of other Microsphaeropsis, the only species which has similar conidia based on conidia size is *M. arundinis*. None of the other Microsphaeropsis (*M. olivaceae, M concentrica, M. centaurae*) bear such small conidia. However, final species identification is not yet complete.

The optimal temperature for growth is 25° C. and the optimal pH for growth is 5.0. There was no marked difference in growth among different media (V-8, PDA (Potato Dextrose Agar) or PDB (Potato Dextrose Broth), Czapek agar or broth, MEA (Malt Extract Agar); PDA, PDB, Czapek and MEA available from either Difco or BBL). The isolate is sensitive to Captan, Mancozeb and Metiram, but is relatively resistant to Myclobutanyl.

Example 2

In vitro Screening

A collection of forty-two fungal isolates were tested for their in vitro ability to degrade apple leaf tissue, inhibit pseudothecia, and ascospore production. Ascospore production was retained as the most useful screening parameter. Six isolates (P176A, P130A, P11A, P164A, P138A and P10A) proved to significantly reduce the ascospore production of *Venturia inaequalis*. Two isolates (P130A and P176A) were as effective as *Athelia bombacina*, a previously reported antagonist of pseudothecia formation and inhibited over 98% of the ascospore production under in vitro conditions.

Leaf disks were cut from non infected apple leaves (cv McIntosh). The leaf disks were sterilized by irradiation (10 hr, 40 kGy of gamma radiation). Glass jars (500) were filled with 100 ml of Perlite™ and 50 ml of distilled water and were then autoclaved for 15 minutes at 121° C. The leaf disks were placed in them under sterile conditions, abaxial surface up, at a rate of 4 disks per jar. The jars were used as sampling units.

The conidia of *V. inaequalis*, (5 isolates), were produced with very slight modifications of previously published methods (Keitt and Palmiter, 1938; Williams, 1976). A mycelial suspension of *V. inaequalis* was made from one-month-old cultures grown on PDA (7 isolates). Each disk received 50 $\mu$L of the conidial (C) or mycelial (M) suspension and were incubated at room temperature in full darkness for approximately two weeks.

The fungal isolates were grown on V8 agar for two weeks. One month after the inoculation with *V. inaequalis*, a mycelial suspension of each fungal isolate was made and applied directly on the leaf disks (50 $\mu$L/disk) of 5 jars. Two uninoculated controls per block were used: sterile disks and *V. inaequalis* inoculated alone. The jars were kept at 25° C. in full darkness for one week to favor antagonist colonization, incubated at 4° C. for a month and then were transferred to 10° C. for an extra 3 months. An isolate of *A. bombacina* found antagonistic in Heye's study (1982) was included as a positive control.

The maximum rupture force (N), per leaf thickness (mm) was recorded for each disk using a Instron® penetrometer using a 50-Newton cell with crosshead speed set at 100 mm/min. All disks were recovered for the following tests.

The ascospore production was measured after a simulated winter. Three different readings at weekly intervals were taken to observe any possible lag in spore maturation. The results of the three extractions are reported for each treatment as the total ascospore production per $cm^2$.

The two remaining disks of each jar were cleared by autoclaving them in glass petri dishes with approximately 25 ml of a KOH solution 0.4M (20 g/L). After careful decantation of the caustic solution, a few drops of lactophenol were added to each disk. The pseudothecia were counted under a binocular at a low magnification, and expressed as the number of pseudothecia per square centimetre.

The *V. inaequalis* control significantly affected leaf rheology as compared to the sterile disk, consequently it served as the reference for the other treatments. Aside from the positive control (*A. bombacina*), a total of ten isolates in the C and twenty-one in the M experiment significantly reduced the leaf strength in vitro at the 95% confidence level. Of these, five of the six best were common to both inoculation methods. Except for the difference between the sterile control and all the treatments, the leaf strengths showed no obvious groupings and varied smoothly with the different treatments. The nine best treatments in the M experiment were not statistically different from one another, and similarly for the nineteen best treatments of the C method.

Aside from the control, three isolates (P130A, P176A and P11A) significantly reduced the ascospore production in the C experiment while six isolates (P176A, P130A, P11A, P164A, P138A and P10A) did the same in the M experiment (FIG. 1 and FIG. 2). The three first isolates are common to both sets. Treatment with P130A is reported by both methods to be as efficient as *A. bombacina*, while P176A is rated similarly only in the M experiment. More than 98% of the ascospore production (>1.84 log reduction) was inhibited by the fungi classed alongside *A. bombacina*.

In the C experiment, 5 isolates (P130A, P11A, P176A, P10A, and 306) aside from the positive control (AB) significantly reduced the pseudothecial production and the efficiency of the first three was not significantly different from *A. bombacina*. A total of nine isolates significantly reduced pseudothecial production.

Example 3

Field Testing

Among our collection of fungal isolates, an isolate of *Microsphaeropsis spp.* has shown the ability to inhibit ascospore production under controlled conditions (in vitro test). In order to estimate the real potential of this antagonist as well as others, tests were conducted under natural condition. The objective of this study was to test the efficacy of fungal isolates in reducing ascospore potential under orchard conditions.

All assays in the field were done at Frelighsburg (Québec) experimental farm of Agriculture Canada. In the beginning of October, apple leaves (*Malus pumila* Mill. "McIntosh") naturally infected with *V. inaequalis* were collected on the trees. This apple variety was chosen for its susceptibility to infections of *V. inaequalis* (Cke.) Wint. The trees had not been sprayed with fungicides and leaves showed severe apple scab symptoms. The leaves were carefully examined and leaves without evident scab lesions were discarded. The leaves were stored at 2° C. in bags until processed. Infected leaves not treated with the fungal isolate were used as control.

The number of ascospores on lesions from naturally infected leaves is extremely variable (0 to more than 2,000 ascospores). This makes the analysis and interpretation of the results difficult. Since increasing the number of leaves sampled would not be possible because of the time required to count the ascospores it was decided to add a test with artificially inoculated apple leaves. Since this method have previously shown to produce more uniform results. Leaf disks were cut in non infected apple leaves collected randomly from McIntosh trees using a stainless steel cork borer of 2.7 cm in diameter (or 5,73 $cm^2$) and sterilized in a glass jar by irradiation (10 hours exposition at 40 kGy (4Mrad) of gamma radiation). Sterile leaf disks were placed in glass jars (4 per jar), filled with 100 ml of Perlite and 50 ml of distilled water and then autoclaved for 15 minutes at 121° C. After cooling of the jars, the leaf disks were placed in jars under sterile conditions, abaxial surface up. A mycelial suspension of *Venturia inaequalis* was made from a 1:1:1:1:1 mixture of cultures originating from 5 different isolates of known sexual compatibility and 50 μl of the mycelial suspension was inoculated on the disks surfaces. The disks were then incubated at room temperature in full darkness for approximately two weeks prior to antagonist inoculation.

The antagonist was grown on potato-dextrose agar at 20° C. until the fungi covered more than approximately half the surface of a 9-cm Petri-dish. They were then stored at 2° C. until the day of application on the leaves or leaf disks. On the day of application, 25 Petri-dishes were cut and inserted in a sterile plastic bag along with 300 mL of distilled water. The bag contents were homogenized in a Stomacher for 480 seconds at normal speed or longer until the same homogeneity was obtained. The bag contents were then transferred to a beaker of 2 L capacity and the volume was adjusted to 1.5 L with distilled non sterile water. Each treatment consisted of applying 500 mL of this preparation to 450 scabbed leaves. The leaf disks artificially inoculated with *V. inaequalis* received 50 μL of a mycelial suspension of the antagonist. After an incubation of two weeks at room temperature leaf disks were placed on the orchard floor.

Each sample of treated leaves or leaf disks were overwintered under screen cages so that leaves were exposed to natural weather conditions. The cages were installed in the orchard in a randomized complete block design and fastened to the ground with wire pegs. The blocks represented different locations in the orchard. Leaf cages remained in the orchard until the end of the ascospore ejection period the following spring.

Figure 3A:
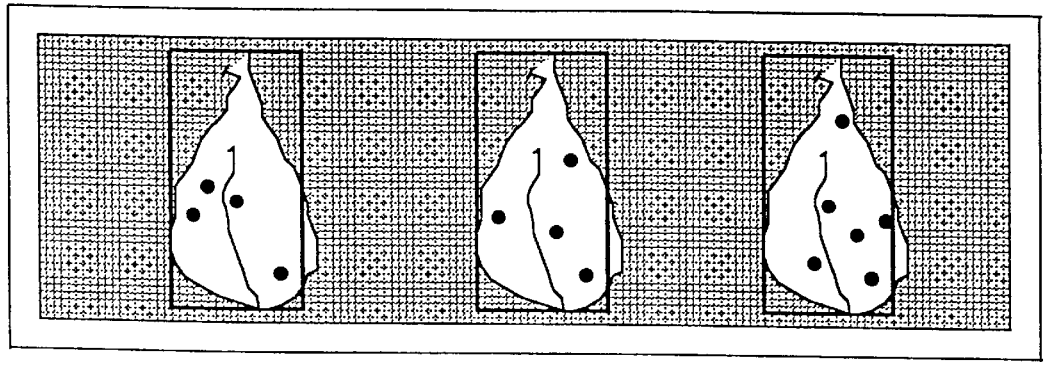
FIG. 3: Wooden cages used for ascospore monitoring.
Figure 3B:
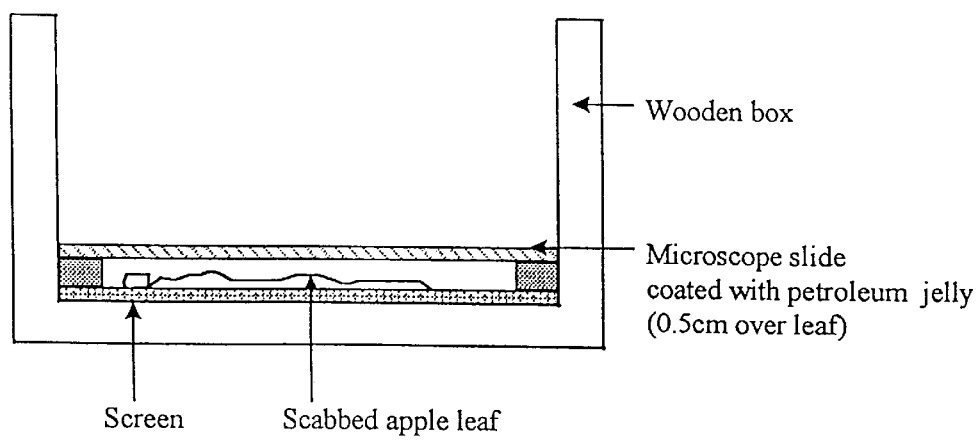

The ascospore production for each treatment was evaluated during the whole ascospore ejection periods, from late April to early July. Three leaves per treatment, randomly chosen, were installed on the bottom of a wooden spore trap (Coulombe 1976); FIG. 3, the ventral face upward. At 0.5 cm above the leaves, microscopic slides, previously coated with petroleum jelly, were installed. After each period of rain, all the microscopic slides were removed and immediately replaced with new ones. These microscopic slides were stored at 0° C. until examination. The number of ascospores present on 40% of the slide surface were counted.

Figure 4:
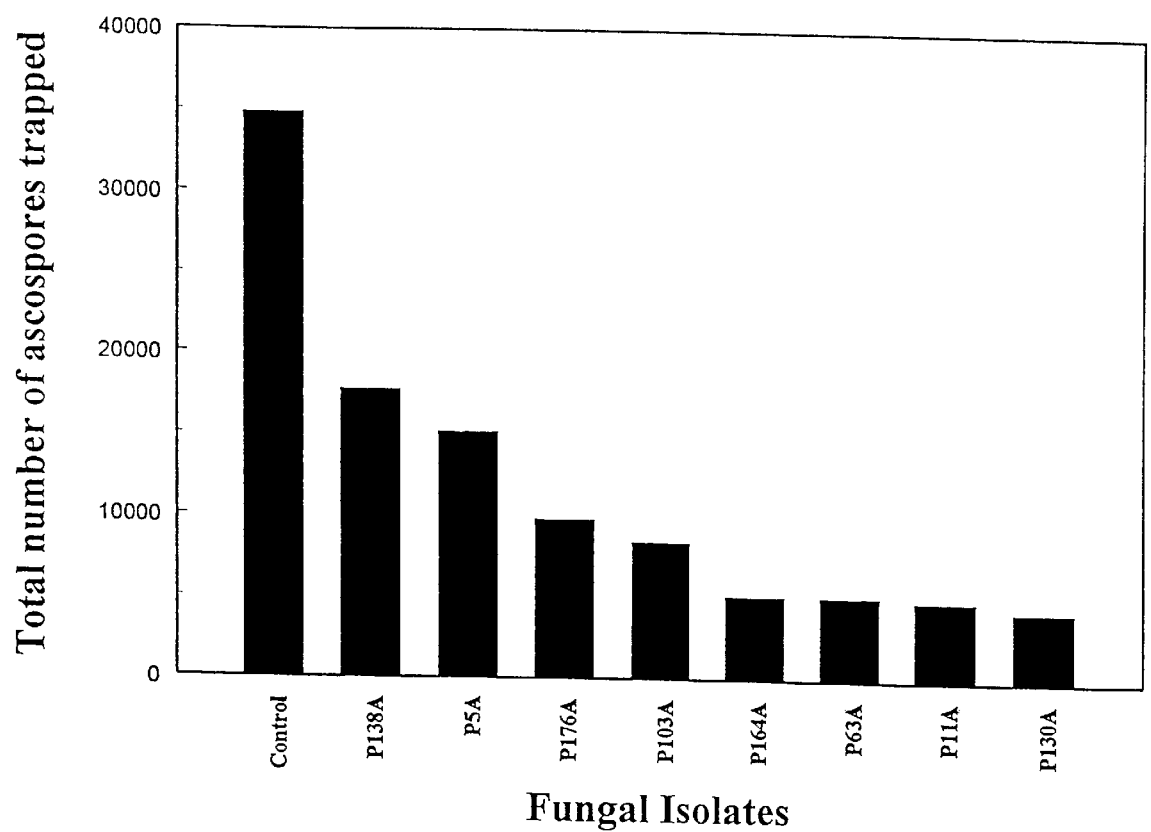
FIG. 4: Effect of fungal isolates on ascospore production on naturally infected apple leaves under orchard conditions.

The isolates labelled P130A reduced the ascospore production by 87% (FIG. 4). The cumulative number of ascospores trapped followed a typical pattern. Looking at each rain event, we observed only three periods with moderate ascospore production as opposed to six in the control.

Figure 5:
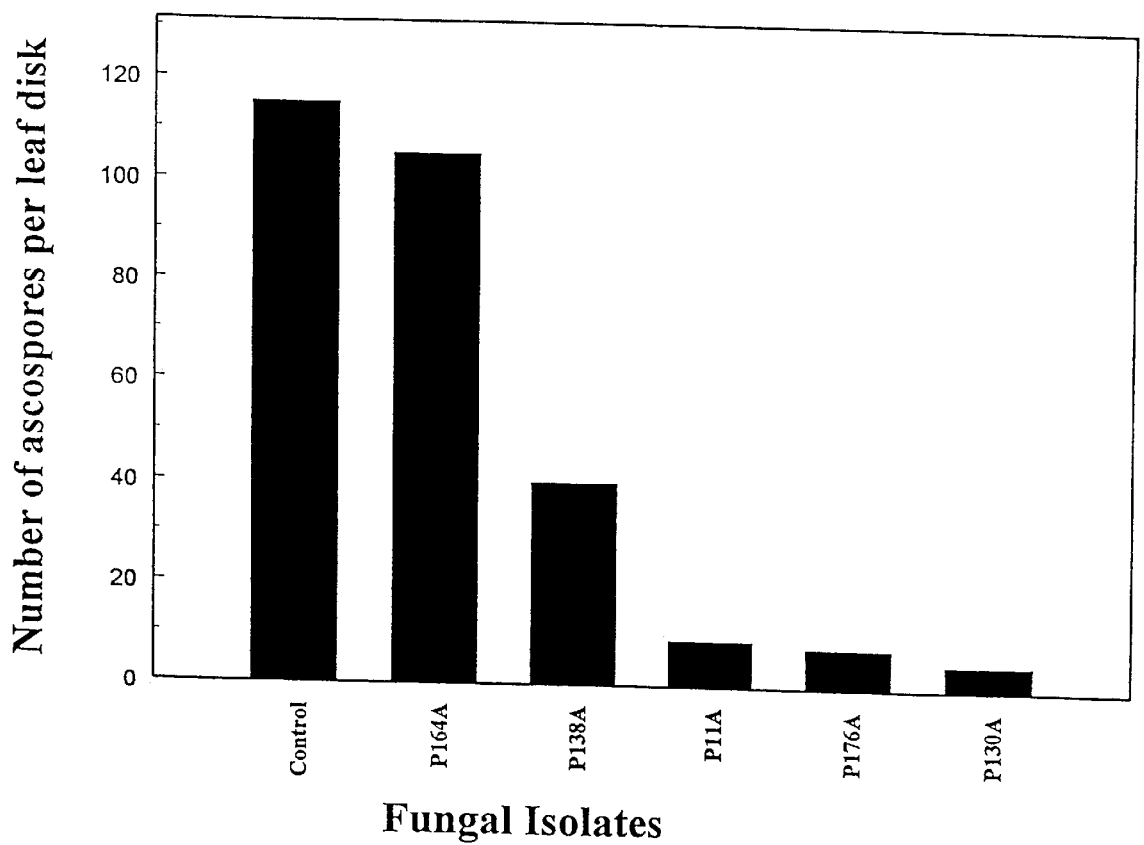
FIG. 5: Effect of fungal isolates on ascospore production on artificially infected apple leaves under orchard conditions.

Because of the inherent variation in ascospore numbers produced on naturally infected leaves, other tests were conducted on artificially inoculated leaves. Half of these leaves were incubated in vitro and the other half in the orchard. The amount of ascospores produced on these leaves was measured only once since mature ascospores accumulated in the pseudothecia in the absence of rain (Philion, 1995). For the isolate P130A, we observed 96 and 95% ascospore inhibition on leaves incubated in vitro and on those placed in the orchard for the whole winter, respectively (FIG. 5). Thus, if we compare the two tests, natural vs artificial infection of leaves with *V. inaequalis*, we can note that in all artificial inoculations including experiments done earlier (Philion, 1995) the ascospore inhibition when leaves are treated with the isolate P130A varies from 95 to 98%. However, when leaves are naturally infected with *V. inaequalis* and maintained under orchard conditions the inhibition is reduced to about 87%. One possible explanation would be that the mycoparasitism activity of the antagonist which implies an intimate contact between the antagonist and the pathogen is favored in artificial inoculations. Natural microbial competition present on leaves naturally infected with *V. inaequalis* may also explain the difference in efficiency since this competition is absent on leaves artificially inoculated.

Example 4
Mode of Action of the Microbial Pest Control Agent

The purpose of the work described here was to determine the mode of action of *Microsphaeropsis sp.* in its antagonism against *V. inaequalis* and other potential pathogens. To this end, two aspects of the interaction between *Microsphaeropsis sp.* and its host was studied: cytological and cytochemical investigation of the interaction and biological activity of extracellular metabolites produced by *Microsphaeropsis sp.*

Cytological aspect of the interaction between *Microsphaeropsis sp.* and its host *Microsphaeropsis sp., Pythium ultimum, Botrytis cinerea, Rhizoctonia solani*, were kept at room temperature on Potato dextrose agar medium (PDA), while *Venturia inaequalis*, was kept at 15° C. on PDA.

Sterile microscopic glass slides (2.5×7.5 cm) were immersed in four time dilute PDA. The next day, discs (5 mm) cut with cork borer from the leading edge of colonies were deposited 3.5 cm apart on slides. Two Petri dishes for each dual culture were incubated for at least 5 days at room temperature. Interactions between the opposing colonies were visualized progressively under reversed light microscopy. Because *V. inaequalis* is a slow grower, *Pythium ultimum, Botrytis cinerea, Rhizoctonia solani* were chosen for preliminary experiments.

In tip-to-host side interactions, the antagonist tips continued to grow after contact; they grew over or along the host hyphae depending on the angle of the contact. A few hours after contact, vacuolation or coagulation of *B. cinerea* and *P. ultimum* hyphae occurred. In some instances, lysis occurred in *P. ultimum* by violent discharge from a narrow region where host and antagonist have first made contact. In *B. cinerea*, the development of intracellular hyphae of *Microsphaeropsis sp.* was observed.

Antifungal activity of extracellular metabolites produced by *Microsphaeropsis sp.*

*Microsphaeropsis sp., Cladosporium cucumerinum, Botrytis cinerea* were both kept at room temperature on Potato dextrose agar medium (PDA), while *Venturia inaequalis*, was kept at 15° C. on PDA.

One liter of malt extract liquid medium was poured into two 1-L Erlenmeyer flask. The medium was inoculated with ten discs of *Microsphaeropsis sp.* grown on solid medium (7-mm diameter) punched out from the edge of a 7-day-old colony grown on PDA. The fungus grew at 26° C. for different periods of time (5, 10, 15, 20, 25, and 30 days), with agitation at 175 rpm. At the end of the incubation period, the mycelium was collected, dried to a constant weight in a ventilated oven at 100° C., and weighed. The pH values of the liquid culture were measured during the course of the experiment.

After discarding the mycelium, the liquid media was extracted three times with one volume of chloroform for one volume of culture filtrate. The chloroform extract was dried under vacuum, with a 40° C. water bath and a rotary evaporator, then was redissolved in chloroform. Chloroform extracts were transferred to 4 ml vials, dried under nitrogen stream and weighed. The dried extracts were resuspended in a known volume of chloroform or methanol.

The screening of molecules with antifungal activity was performed with thin layer chromatography (TLC). TLC was carried out for analytical purpose with silica gel plates (Merck 60 $F_{254}$, 0.2-mm thick). Chloroform extracts were deposited as spots of 50 $\mu$l after drying, the chromatograms were developed in an appropriate solvent mixture. The spots were viewed under ultraviolet radiation at 254 and 366 nm. To localize zones with antifungal activity, silica gel plates were seeded with a sporal suspension of *Cladosporium cucumerinum*. Because of the dark pigmentation of spores and mycelium of this fungus, zones of antifingal activity could be readily identified as white spots. Spraying of sporal suspension of *C. cucumerinum* minimally revealed two major active spots in the chloroform extract with an approximately $R_f$ value of 0.65 and 0.95.

For a large scale purification, chloroform extracts were purified by silicic acid column chromatography. The extracts were applied to a column (2×37 cm) filled with silica gel silicic acid (Silica Gel; 60-230 mesh, Baker Analyzed reagent) and flash-chromatographed by successive elutions with steps of increasing concentration of methanol in chloroform: 0, 2.5, 5, 10, 30, 50, 100%. For each eluted fraction, assessment of antifungal activity was carried out with the TLC bioassay as described above. Different products were found in different mixtures of chloroform/methanol. Fractions containing the same products, as determined by TLC plate, were pooled for further analysis. The active fraction was designated F-II.

The fraction F-II was further purified by preparative thin layer chromatography silica gel 60 $F_{254}$ 0.5 mm (Merck). The chloroform fraction FII was deposed on the plate (20×20 cm), which was developed using the solvent system $CH_3Cl$:AcEt (1:1; v/v). The fractions F-II1; F-II2; F-II3a and F-II4a were extracted from silicic acid with chloroform and the fractions F-II3b; F-II4b were extracted with methanol. Thin layer bio-assay revealed the antifungal activity in F-II2 ($R_f$=0.46) and F-II3a ($R_f$=0.34).

Aliquots of the semi-purified chloroformic extract (Fraction F-II3a) were added to 10-ml vials and dried by sterilized air to remove the solvent. The residue was weighed, and the vials were filled with 2 ml of potato dextrose broth (PDB) and inoculated with 7-mm disc of *B. cinerea* or *V. inaequalis*. Antifungal activities were determined by weighing the colonies as described above.

Growth of the fungus, pH of the medium, and antiflngal activity of the culture filtrates were determined for 30 days of culture. During the growth period, the pH value stayed relatively stable. The antifungal activity was detectable after 15 days, and reached a maximum after 20 days of culture under our standard conditions. On silica gel thin layer chromatograms, chloroform extracts were separated into several spots as visualized under ultraviolet radiation at 254 and 366 mm and by cerric sulfate ammonium molybdate reagent.

Example 5

Field Trials

The biological control agent in a suspension of $4.5\times10^5$ conidia per ml was applied at a rate of 1125 L/ha or 1.2 L per tree. The suspension was applied using conventional orchard sprayers.

The suspension was applied in one of two methods, either after apple harvest but before leaf fall or in two applications on the ground at about 60% and 90% leaf fall.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiments of the invention in which an exclusive property of privilege is claimed are defined as follows:

1. A method of controlling apple scab caused by *V. inaequalis* comprising applying an effective amount of an isolate of a species of the genus Microsphaeropsis to apple leaf or leaf litter.

2. The method of claim 1, wherein the isolate is P130A, ATCC deposit 74412.

3. The method of claim 2, wherein the effective amount of the isolate is from $2\times10^5$ to $6\times10^5$ conidia per ml.

4. The method of claim 3, wherein the isolate is applied at a rate of from 1000 L/ha to 1500 L/ha.

5. The method of claim 3, wherein the isolate is applied at a rate of from 1.0 L/tree to 1.5 L/tree.

* * * * *